(12) United States Patent
Slivka et al.

(10) Patent No.: US 7,294,617 B2
(45) Date of Patent: Nov. 13, 2007

(54) METHOD FOR NONSURGICAL TREATMENT OF THE INTERVERTEBRAL DISC AND KIT THEREFOR

(75) Inventors: Michael Andrew Slivka, Taunton, MA (US); Hassan Serhan, Easton, MA (US)

(73) Assignee: DePuy Acromed, Inc., Raynham, MA (US)

( * ) Notice: Subject to any disclaimer, the term of this patent is extended or adjusted under 35 U.S.C. 154(b) by 0 days.

(21) Appl. No.: 10/938,197

(22) Filed: Sep. 9, 2004

(65) Prior Publication Data

US 2005/0038518 A1    Feb. 17, 2005

Related U.S. Application Data

(62) Division of application No. 10/102,075, filed on Mar. 19, 2002, now Pat. No. 6,812,211.

(51) Int. Cl.
*A61K 38/00* (2006.01)

(52) U.S. Cl. ........................................ 514/12; 424/69.1

(58) Field of Classification Search ................... 514/12
See application file for complete search history.

(56) References Cited

U.S. PATENT DOCUMENTS

| | | | |
|---|---|---|---|
| 4,600,739 A | 7/1986 | Krankkala | |
| 4,716,224 A | 12/1987 | Sakurai | |
| 4,931,546 A | 6/1990 | Tardy | |
| 5,024,742 A | 6/1991 | Nesburn | |
| 5,306,500 A | 4/1994 | Rhee | |
| 5,510,418 A | 4/1996 | Rhee | |
| 5,972,385 A | 10/1999 | Liu | |
| 6,126,682 A | 10/2000 | Sharkey | |
| 6,165,488 A | 12/2000 | Tardy | |
| 6,165,758 A | 12/2000 | Asai | |
| 6,187,048 B1 | 2/2001 | Milner | |
| 6,206,921 B1 | 3/2001 | Guagliano | |
| 6,231,608 B1 | 5/2001 | Stone | |
| 6,605,570 B2 | 8/2003 | Miller | |
| 6,624,245 B2 | 9/2003 | Wallace | |
| 2002/0049498 A1 | 4/2002 | Yuksel | |
| 2002/0176893 A1* | 11/2002 | Wironen et al. ............. | 424/489 |
| 2003/0049301 A1 | 3/2003 | Hedman | |
| 2003/0181365 A1 | 9/2003 | Slivka | |
| 2004/0054414 A1* | 3/2004 | Trieu et al. ............... | 623/17.16 |
| 2004/0253219 A1 | 12/2004 | Hedman | |

FOREIGN PATENT DOCUMENTS

| | | |
|---|---|---|
| WO | 95/34332 | 12/1995 |
| WO | WO97/26847 | 1/1997 |
| WO | WO 00/20021 | 7/1999 |
| WO | WO 00/62832 | 10/2000 |
| WO | 01/07009 | 1/2001 |
| WO | WO 01/76654 | 4/2001 |
| WO | WO 01/70151 | 9/2001 |
| WO | WO 03/020031 | 8/2002 |

OTHER PUBLICATIONS

Fumihiko, Kato, Med et al, Serial hanges Observed by Magnetic Resonance Imaging in the Intervertebral Disc After Chemounucleolysis- A Consideration Of The Mechanism of Chemonucleotysis; Department of Orthopaedic Surgery, School of Medicine, Nagoya University,Nagoya City, Japan, May 20, 1991.
Juergen Kraemer, , MD & Heiko Laturnus MD; Lumbar Intradiscal Instillation With Aprotinin; SPINE vol. 7, No. 1, 1982; pp. 73-74; 1982 Harper & Row Publishers, Inc.
Eugene Khor; Methods of Treatment of Collagenous Tissues for Bioprostheses; Biomaterials 18 (1997) pp. 95-105; Elsevier Science Limited.
C.P. Pathak et al., Water Soluble Tissue Crosslinkers for Bioprostheses; 2001 Society for Biomaterials; 27th Annual Meeting Transactions.
Gunner, Do Human Lumbar Discs Reconstitute After Chemonucleolysis, Spine, 1999, pp. 342-248, vol. 24, No. 4, Lippincott, Williams & Wilkins, Inc.
Krugluger, Chemonucleolysis and and automated percutaneous discectomy-a prospective randomized comparison, International Orthopaedics, 2000, vol. 24, pp. 167-169, Springer-Verlag.
Mwale, Biological evaluation of chitosan salts cross-linked genipin as a cell scaffold for disk tissue engineering, Tissue Eng., 2005, Jan.-Feb. 11 (1-2):130-40.

* cited by examiner

*Primary Examiner*—Cecilia J. Tsang
*Assistant Examiner*—Maury Audet
(74) *Attorney, Agent, or Firm*—Thomas M. DiMauro

(57) ABSTRACT

This invention relates to a method and compositions for treating pathological intervertebral discs comprising the step of delivering an agent that causes chemical crosslinking of the native molecular components of the disc. Supplemental materials which are susceptible to crosslinking by the aforementioned agent are optionally delivered to the disc in order to increase and maintain disc height.

7 Claims, No Drawings

METHOD FOR NONSURGICAL TREATMENT OF THE INTERVERTEBRAL DISC AND KIT THEREFOR

CONTINUING INFORMATION

This application is a divisional application of U.S. Ser. No. 10/102,075, filed Mar. 19, 2002 (Slivka et al.) now U.S. Pat. No. 6,812,211, entitled "Method for Nonsurgical Treatment of the Intervertebral Disc and Kit Therefor".

BACKGROUND OF THE INVENTION

The intervertebral disc contains three major components: a nucleus pulposus (a fluid-like component comprising proteoglycans and collagen), an annulus fibrosis (a flexible, collagen-based ring surrounding the nucleus pulposus) and a pair of cartilaginous endplates which help enclose the nucleus pulposus within the annulus fibrosus. A normal, healthy nucleus pulposus acts much like a pressurized fluid by transferring and distributing compressive load to the annulus fibrosis, thereby causing a slight expansion of the annulus fibrosus. However, injury and/or degeneration of the intervertebral disc in the human spine can be caused by disc herniation, rupture of the annulus, prolapse of the nucleus pulposus, mechanical instability of the disc and/or dehydration of the disc, thereby leading to back pain. In addition, damage or degeneration of the annulus fibrosus in the form of a herniation, tear and/or crack reduces its ability to resist the tensile stresses conferred by the nucleus pulposus. Thus, the disc experiences excessive bulging that may result in spinal cord and/or nerve root impingement and subsequent back pain. Further, the nucleus pulposus can leak into the foramenal spaces, causing irritation of nerve roots and foramenal stenosis.

Treatments such as discectomy, laminectomy, laminotomy and/or spine fusion procedures represent state of the art surgical treatment for disc problems. Typically, the goal of these treatments is to relieve pressure on the neural elements by eliminating the material causing stenosis or irritation of the neural elements. However, discectomy when performed alone can result in significant loss of disc height and frequently provides only temporary pain relief. Laminectomy/laminotomy procedures also provide only temporary relief by opening up the spinal canal and decompressing the spinal cord, which is susceptible to restenosis due to scar tissue formation at the operative site. Spine fusion is considered by some to be a last resort, "most" invasive procedure that eliminates the flexibility of the motion segment and usually involves permanent hardware implantation. Furthermore, fusing spinal segments has been linked to adjacent level disc degeneration. All of these techniques have the disadvantage that they require surgical intervention to carry out the treatment.

Percutaneous microdiscectomy has been suggested as a minimally invasive discectomy procedure but still carries the disadvantage of causing disc height loss. Chemonucleolysis has been used clinically for decades and relieves pressure on a disc herniation by breaking down the nucleus pulposus. In essence, chemonucleolysis is a chemical discectomy. Because the goal of this treatment is to basically digest the nucleus, the consequent reduction in viscosity of the nucleus pulposus makes it more susceptible to leakage. In addition, this procedure appears to be associated with a 1%, incidence of anaphylaxis which has caused patient deaths. Furthermore, the procedure is known to also cause disc height loss.

Because of the drawbacks associated with the conventional procedures, newer procedures have been developed with an aim towards relieving back pain without requiring invasive surgery and without reducing disc height and providing a longer-lasting therapeutic effect.

Injecting curable or hardening materials into the disc following discectomy has been suggested in order to provide a filler material for the space left by removal of the nucleus and/or annular defect. U.S. Pat. No. 6,206,921 ("Guagliano") discloses a method of first removing the nucleus pulposus and/or herniated portion of the annulus fibrosis, then injecting a heated, resilient, natural rubber material that hardens upon cooling. U.S. Pat. No. 6,187,048 ("Milner") discloses an in situ polymerizable nucleus pulposus replacement material that may be enclosed by an impermeable container to prevent leakage. However, these materials may be susceptible to leakage out of the nucleus pulposus if no balloon or sheath has been formed around the material, particularly if the annulus fibrosis has not been adequately repaired. Furthermore, the implant may be subjected to repeated loads exceeding its strength over the lifetime it is expected to function in the patient. The potential consequence of failure is generation of foreign particulate, which has been linked to osteolysis and chronic foreign body reactions.

Other treatment options, which do not require discectomy or nucleotomy, have also been explored. U.S. Pat. No. 6,126,682 ("Sharkey") discloses a method of treating annular fissures by delivering energy and/or materials to localized places near the inner wall of the annulus fibrosus, particularly at the posterior margins, using a functional element. Heating the disc has the potential to "weld" defects and/or shrink disc tissues. However, the mechanism of heating the disc to weld defects is not well understood and may cause secondary problems such as tissue necrosis and nerve root damage. Sharkey also discloses delivering dissolved collagen, adhesives, cements or hydrogels to seal fissures in the annulus fibrosus using the surgical instrument and functional element. However, this delivery is restricted to local points along the inner wall of the annulus fibrosus for treating annular fissures.

Sharkey does not disclose providing a crosslinking agent in an amount effective to cause the crosslinking of any native molecular proteins of the disc, nor does Sharkey disclose depositing a sealant material into the center of the nucleus pulposus portion of the disc.

PCT Publication No. WO 00/62832 ("Haldimann") discloses an in situ curable sealant material that repairs defects in the disc annulus to prevent leakage of nucleus pulposus material. In some embodiments, Haldimann discloses that the sealant material is made of two precursor components: a buffered protein solution (including collagen) and a bifunctional crosslinking agent (including PEG with an activated terminal group). Typically, this injectable material adheres to the surrounding tissues by mechanical interlocking. In some embodiments, Haldiman discloses that covalent bonds are formed between the preferred hydrogel bio-compatible material and the surrounding annulus fibrosus tissue to further increase and secure the attachment of the sealant to the annulus fibrosus tissue in the proximity to the defect in the annulus fibrosus. There is also disclosed a method of adding "artificial nucleus pulposus material" to achieve a volume comparable to a normal nucleus pulposus followed by sealing the annulus.

Haldiman does not disclose providing the crosslinking agent in an amount effective to cause the crosslinking of any of the native molecular proteins of the disc. Haldiman does not disclose depositing the sealant material into the nucleus pulposus.

PCT Patent Publication No. WO 01/70151 ("Aksan") discloses a method of strengthening and stabilizing collagenous tissues comprising the steps of heating to shrink the collagen followed by crosslinking with a non-toxic agent. The treatment is mainly focussed on glenohumeral instability and loose skin problems, but application of capsular shift procedures used to repair injuries of the spine is also mentioned. However, the crosslinking treatment always follows a thermal shrinkage step in the disclosed procedure. Thermal shrinkage is very difficult to achieve in the intervertebral disc beyond a local region without inducing damaging effects and is likely to cause a highly nonuniform tissue morphology. The crosslinking described is focused on collagen molecules, which exist in relatively small proportions in the nucleus pulposus of the spine (~5%).

Aksan does not specifically disclose injecting the crosslinking agent into the intervertebral disc portion of the spine. Aksan does not disclose any method of crosslinking an untreated protein component of the disc.

U.S. Pat. No. 4,931,546 ("Tardy") discloses a method for crosslinking collagen comprising exposing the collagen to a solution of periodic acid or a periodate, then allowing spontaneous crosslinking to occur from the aldehyde groups formed during exposure. Similarly, U.S. Pat. No. 5,972,385 ("Liu") discloses a method of oxidizing polysaccharides, then reacting the oxidized product with collagen and adding a growth factor, and discloses application of material so formed in spinal fusion augmentation. Neither Tardy nor Liu describes in situ crosslinking of native living tissues, particularly in the spine or intervertebral disc.

Accordingly, there is a need for a minimally invasive method of treating pathological intervertebral discs that relieves back pain and encourages long-term disc stability and pain prevention by maintaining disc height, preventing nucleus leakage posteriorly, relieving pressure on a disc herniation, and inducing less alteration of the normal spine biomechanics.

SUMMARY OF THE INVENTION

In accordance with the present invention, there is provided a method of treating a pathologic intervertebral disc wherein a crosslinking agent is delivered to the disc in an amount sufficient to cause the chemical crosslinking of at least a portion of the unmodified native proteins present in the disc. The crosslinking stabilizes and stiffens the disc structure, which has the therapeutic effect of relieving pressure on neural elements such as the spinal cord and the exiting nerve roots. The stabilization also prevents prolapse of the nucleus material, thereby preventing foramenal stenosis and loss of disc height. The invention further provides a least-invasive medical treatment for injured and/or degenerated intervertebral discs that will hopefully maintain most of the flexibility and functional biomechanics of the normal disc and prolong the need for surgical intervention.

The present invention involves crosslinking the native molecular components of the intervertebral disc, rather than removing or dissolving them. The potential effects of crosslinking are multi-fold, including altering the biomechanical nature of the nucleus pulposus from a viscous gel to a viscoelastic solid, thereby preventing prolapse into the spinal canal and reducing the tendency for excessive bulging of the annulus fibrosis, which are primary suspects for causing low back pain and sciatica. Crosslinking also inhibits the degradation of the disc by providing stable, durable chemical bonds, which can help maintain disc height and prevent excessive motion of the disc level, again preventing painful pinching of the nerves and rupture of the annular fibers. The present invention can be performed as an outpatient procedure and does not require surgical intervention, and so is particularly useful as a minimally invasive, early intervention strategy.

Therefore, in accordance with the present invention, there is provided A method of treating in a living being an intervertebral disc having a nucleus pulposus, comprising the step of:
 a) injecting a crosslinking agent into the nucleus pulposus.

Also in accordance with the present invention, there is provided method of treating in a living being an intervertebral disc having a nucleus pulposus, an annulus fibrosus, and native proteins, comprising the step of:
 a) injecting an effective amount of a crosslinking agent into the intervertebral disc to cause in situ crosslinking of at least a portion of the native proteins present in the disc

DETAILED DESCRIPTION OF THE INVENTION

For the purposes of the present invention, a "native protein" is any protein possessing any native elements. Accordingly, a native protein may have a synthetic functional group produced by reaction with a foreign agent and still be considered a native protein. An "unmodified protein" is a protein which has not been subjected to heat in an amount sufficient to shrink the Collagen therein.

The intervertebral disc comprises three major components: 1) the nucleus pulposus, 2) the annulus fibrosus, and 3) a pair of cartilaginous endplates. The present invention may be practiced upon any of these sites, alone or in any combination.

Preferably, the nucleus pulposus portion of the intervertebral disc is selected as the target site for the chemical crosslinking of the proteins therein. Treating the nucleus pulposus with the method of the present invention can stiffen the nucleus pulposus (thereby reducing undesired mobility), and prevent native material within the nucleus pulposus from leaking out. In some embodiments, the crosslinking agent is injected only into the, nucleus pulposus. When the crosslinking agent is injected into the nucleus pulposus, it is preferred that the agent be injected into the center of the nucleus pulposus.

In some preferred embodiments, both the nucleus pulposus and the annulus fibrosis may be, treated with the same injection of crosslinking agent. Still more preferably, the injection causes not only the crosslinking of substantially the entire bulk of the nucleus pulposus, but also the crosslinking of the periphery of the nucleus pulposus to the inner wall of the annulus fibrosus. When this embodiment is practiced, it is preferred that the agent be injected only into (and preferably into the center of) the nucleus pulposus, and that light exercise be performed by the patient in order to disperse the agent to the periphery of the nucleus pulposus.

In other preferred embodiments, only the annulus fibrosis is treated. Treating the annulus fibrosus with the method of the present invention can have the effect of binding a tear in the annulus fibrosus. When this embodiment is practiced, it is preferred that the agent be injected into the defect produced by the tear.

In some procedures, compositions of the present invention may be first injected into a first site in the disc, and then injected into a second site in the same disc. For example, a probe can be first manuevered into the disc and positioned so that a composition of the present invention may be first delivered only into the nucleus pulposus portion of the disc. The probe can then be manuevered again within the disc and positioned so that the same (or a different) composition of the present invention may be delivered to a defect in the annulus fibrosus.

In some patients having a disc characterized by advanced degeneration, the line of demarcation between the annulus fibrosus and the nucleus pulposus becomes unclear. Accordingly, in these cases, the crosslinking agent is preferably injected into the center of the disc.

The nucleus pulposus typically contains more than 80 volume percent (vol %) water (depending on age and condition). The protein content of the nucleus pulposus typically comprises approximately 50 weight percent (wt %) proteoglycans, 20 wt % collagen (mainly Type II collagen), and other small proteins such as fibronectin, thromospondin, and elastin. The water and proteoglycan content of the nucleus pulposus generally decreases with age and onset of pathological changes. Hence, they are expected to be present in lower amounts in the intervertebral discs in patients that are candidates for the method of this invention.

The annulus fibrosis is generally slightly less hydrated than the nucleus pulposus and its protein content comprises about 15 wt % proteoglycan and 70 wt % collagen (mainly Type I collagen). The annulus fibrosis may also lose water with age and disease, but generally experiences more structural changes, such as tearing and formation of thick bundles, than biochemical changes.

The cartilaginous endplate is a thin layer of hyaline cartilage similar to articular cartilage and dry weight is composed of mainly Type II collagen.

When the nucleus pulposus site is so selected, it is preferred that the crosslinking agent be selected so that it effectively causes the crosslinking of at least the proteoglycan protein component thereof (as it is the predominant protein in nucleus pulposus). It is more preferred that the crosslinking agent be selected so that it effectively causes the crosslinking of both the proteoglycan and collagen protein components thereof (as collagen is the second most predominant protein in nucleus pulposus). However, in some embodiments, the crosslinking agent is selected so that it effectively causes the cross linking of the collagen protein component thereof. In other embodiments, the crosslinking agent be selected so that it effectively causes the crosslinking of essentially all the protein components of the nucleus pulposus. When the annulus fibrosus site is so selected, it is preferred that the crosslinking agent be selected so that it effectively causes the cross linking of at least the collagen protein component thereof (as it is the predominant protein in annulus fibrosus). It is more preferred that the crosslinking agent be selected so that it effectively causes the crosslinking of both the proteoglycan and collagen protein components thereof (as proteoglycan is the second most predominant protein in the annulus fibrosis). However, in some embodiments, the crosslinking agent is selected so that it effectively causes the crosslinking of the proteoglycan protein component of the annulus fibrosus. In other embodiments, the crosslinking agent is selected so that it effectively causes the crosslinking of essentially all the protein components present at the defect of the annulus fibrosus.

Chemical crosslinking of the selected molecular components can be accomplished, using a variety of methods, including both direct and indirect crosslinking processes. Typically, crosslinking of proteins is accomplished when an aldehyde functional group reacts with an amino acid group to form a bond therebetween. In some embodiments of the present invention involving aldehyde and amino acid functional groups, the aldehyde functional group may be either synthesized upon a native protein or provided by a foreign agent, while the amino acid functional group is either present upon a native protein or provided by a foreign agent, provided that at least one of the functional groups is present on a native protein.

For the purposes of the present invention, a crosslinking agent may "cause" the crosslinking of proteins by methods including but not limited to:

a) directly chemically bridging two functional groups from two different protein molecules ("inter-protein direct crosslinking");

b) directly chemically bridging two functional groups from the same protein molecule ("intra-protein direct crosslinking");

c) reacting with a first protein molecule to form a synthetic functional group on a first protein molecule (typically an aldehyde) which in turn reacts with a second functional group (typically an amino acid group) on a second protein molecule ("inter-protein indirect crosslinking"); or d) reacting with a protein molecule to form a synthetic functional group on the protein molecule (typically an aldehyde) which in turn reacts with a second functional group (typically an amino acid group) on the same protein (intra-protein indirect crosslinking).

Accordingly, in some embodiments, the in-situ crosslinking of the native proteins is accomplished by crosslinking a first synthetic functional group and a second functional group within a single native protein molecule. In some embodiments, the single native protein molecule is a proteoglycan, while in others the single native protein molecule is collagen. In general, aldehyde groups do typically not exist on native proteins. Accordingly, they must be provided as either a synthetic functional group (e.g., by using an oxidizing agent upon a protein) upon a native protein, or as a functional group of a foreign agent.

In other embodiments, the in-situ crosslinking of the native proteins is accomplished by crosslinking a first functional group of a first protein molecule with a second functional group of a second protein molecule. In some embodiments, the first protein molecule is the same type as the second protein molecule. In some cases thereof, the first and second protein molecules are Type I collagen, while in others the first and second protein molecules are Type II collagen, and in still others the first and second protein molecules are a type of proteoglycan. In some embodiments, the first protein molecule is a different type than the second protein molecule. In some embodiments thereof, the first protein molecule is a type of collagen and the second protein molecule is a proteoglycan. In other embodiments thereof, the first protein molecule is Type I collagen and the second protein molecule is Type Il collagen. In other embodiments thereof, the first protein molecule is a glycosaminoglycan and the second protein molecule is Type II collagen.

Direct crosslinking can be used in accordance with the present invention, and typically involves using the crosslinking agent as a bridge to chemically connect one amino acid group on one protein molecule to another amino acid group on the same or different protein molecule. These agents are called bifunctional agents. In some preferred embodiments, the crosslinking agent comprises a pair of functional groups that react with amino acid groups on the native proteins to be linked. Preferably, these functional groups are aldehydes.

Direct crosslinking can be accomplished in either conventional one step or multi-step procedures. Conventional methods of direct crosslinking are described by Khor (Biomaterials 18:95–105, 1997), which discloses methods for crosslinking collagenous tissues to improve durability, particularly transplant tissues from xenogeneic or allogeneic sources. In some embodiments of the present invention, direct crosslinking is accomplished in a one-step reaction, preferably by using a bifunctional agent, In some embodiments, the bifunctional agent is selected from the group consisting of dialdehydes, polyepoxy compounds and diisocyanates. One more preferred bifunctional agent used in accordance with the present invention is gluteraldehyde.

Conventional, multistep, direct, crosslinking reactions are also described by Khor. In some embodiments using multistep reactions, the bifunctional crosslinking agent is selected from the group consisting of acyl azide and carbodiimides.

Pathak et al. (Soc for Biomaterials $27^{th}$ Annual Meeting Transactions p. 130, 2001) describe an alternative to gluteraldehyde fixation of bovine pericardium using bis(sulfosuccinimidyl suberate) as the bifunctional agent. It is believed that bis(sulfosuccinimidyl suberate) may be less toxic than gluteraldehyde and is better resistant to calcification.

Crosslinking agents can also be made by attaching functional groups to synthetic polymers, which may improve biocompatibility. One particular example is functionally activating poly(ethylene glycol) with aldehyde groups to manufacture an agent that will directly crosslink tissues in a manner similar to gluteraldehyde and formaldehyde.

Preferably, the direct crosslinking agent of the present invention has a molecular weight of no more than 1 million Daltons. Above this preferred value, the crosslinking agent may be insoluble in water and may be very difficult to inject and disperse into the disc tissues. More preferably, the crosslinking agent has a molecular weight of between about 100 Daltons and about 100,000 Daltons. When the molecular weight of the agent is below about 100 Daltons, the agent may too easily diffuse into bodily tissues outside of the intervertebral disc. When the molecular weight of the agent is above about 100,000 Daltons, the agent may not disperse adequately within the disc tissues to cause uniform crosslinking of native molecules.

One preferred embodiment of this invention involves the direct, one step, aqueous reaction of a water-soluble, bifunctional crosslinking agent with at least a portion of the native proteins of the intervertebral disc. Preferred crosslinking agents for this method include gluteraldehyde, bis(sulfosuccinimidyl suberate), polyepoxy compounds and bifunctionally activated synthetic polymers such as poly(ethylene glycol) dialdehyde. Preferably, the agent is diluted in a pH buffered physiological saline prior to administration. A buffered pH environment is desirable to maintain favorable reaction conditions during crosslinking.

Gluteraldehyde is particularly preferred as a crosslinking agent due to its medical history of use with biolological transplant tissues and injectable adhesives. Preferably, the crosslinking agent (which, is preferably gluteraldehyde) is delivered to the disc in a concentration of between approximately 0.1 and 20 volume percent (vol %), more preferably between 1 and 10 vol % in saline buffered to a pH of approximately 6.5 to 8.0, more preferably between approximately 7.0 to 7.5.

Another method of causing the crosslinking of native intervertebral disc molecular components is to chemically react target portions of native proteins (such as native collagen and/or native proteoglycan proteins) such that synthetic functional groups (such as aldehydes) are created directly on the native proteins. Crosslinking then preferably occurs between the synthetic functional groups (such as aldehyde groups) of the reacted native protein and an unreacted functional group (such as an amino acid group) located on either the same native protein or another molecule. Modification of the native component to form a functional group such as an aldehyde can be achieved using enzymatic oxidizing agents, and are preferably selected from the group consisting of lysine oxidase, transglutaminase, and multi-copper oxidases. Proteoglycans contain polysaccharide regions that may be modified to form aldehyde functional groups. This modification of proteoglycans may be accomplished by using either enzymatic or non-enzymatic agents. Examples of enzymatic polysaccharide oxidizing agents include catechol oxidase and tyrosinase. Examples of non-enzymatic polysaccharide oxidizing agents include periodate ions (periodic acid, sodium and potassium periodate), nitroprusside ions (sodium nitroprusside) and hydrogen peroxide.

In a preferred embodiment of this invention, a non-enzymatic polysaccharide oxidizing agent is injected into the nucleus pulposus of a pathological intervertebral disc. Because the dry weight component of the nucleus pulposus is rich in proteoglycans, there are numerous sites that can be oxidized to form functional aldehydes. Subsequently, the aldehydes can react with amino acid regions of both native collagens and native proteoglycans to form crosslinks.

Chemical modification of proteoglycans, particularly the sulfated proteoglycans, in the nucleus pulposus can elicit the added benefit of reducing the swelling pressure in the nucleus, thereby reducing both the potential for exuding out of the disc and the tendency for the nucleus pulposus to cause bulging of the annulus. This is one proposed mechanism for the effectiveness of chemonucleolysis in reducing pain in properly selected patients (Kato el al., *Spine* 17:934–939, 1992). Furthermore, this mechanism is the basis for clinical experiments conducted with aprotinin, a protease inhibitor that forms strong complexes with sulfated glycosaminoglycans (Kraemer et al., *Spine* 7:73–74, 1982).

Preferably, the indirect crosslinking agent of the present invention has a relatively low molecular weight, is substantially completely reacted in the crosslinking process, and forms by-products (such as gases and water) which can relatively easily exit the reaction site.

As is frequently the case with pathological intervertebral discs, concomitant with the presence of pain is a narrowing of the disc space and/or exuding of disc material (herniation) into the neural foramen. Likewise, the quantity of native tissue present in the disc may be lower than desired in order for crosslinking to restore the stability, biomechanics and disc height desired. Therefore, it may be desirable to add a supplemental protein into the disc as an adjunct to the crosslinking treatment. Preferably, the supplemental protein can be crosslinked by the same crosslinking agent used to crosslink the native proteins of the disc. Examples of supplemental proteins that are useful with the crosslinking strategies described above include but are not limited to collagen in various types and forms, hyaluronan, chondroitin sulfate, keratan sulfate, albumin, elastin, fibrin, fibronectin and casein.

Although it is within the scope of the invention for the supplemental protein to be added before or after the crosslinking step, a preferred embodiment comprises the steps of first adding the supplemental material, then allowing or effecting the dispersion of the material into the disc space, then adding the crosslinking agent. Ultimately, this helps provide a more homogeneous crosslinked structure.

Therefore, in accordance with the present invention, there is provided a method of treating in a living being an intervertebral disc having native molecular proteins, comprising the steps of:
  a) injecting a supplemental protein into the intervertebral disc, and
  b) injecting a crosslinking agent into the intervertebral disc.

In preferred embodiments, the method comprises the sequential steps of:
  a) injecting a supplemental protein into the intervertebral disc,
  b) optionally dispersing the supplemental protein throughout at least the nucleus pulposus portion of the disc, and
  c) injecting a crosslinking agent into the intervertebral disc.

Preferably, the crosslinking agent is injected in an amount sufficient to crosslink at least a portion of the native proteins. More preferably, the crosslinking agent is injected in an amount sufficient to crosslink at least a portion of the supplemental protein. In some embodiments, the supplemental protein is selected from the group consisting of collagen, hyaluronan, chondroitin sulfate, keratan sulfate, albumin, elastin, fibrin, fibronectin and casein. Preferably, when direct crosslinking is performed, the supplemental protein is collagen, and gluteraldehyde is preferably selected as the crosslinking agent. Preferably, when indirect cross linking is performed, a supplemental agent is injected; wherein the agent is a polysaccharide (more preferably, hyaluronan) and sodium periodate is preferably selected as the crosslinking agent (which functions as a polysaccharide oxidizing agent). In some embodiments, the supplemental protein is injected substantially into the nucleus pulposus. More preferably, the crosslinking agent is also injected substantially into the nucleus pulposus. Because the supplemental protein can react with the crosslinking agent, in preferred embodiments, the crosslinking agent is provided in first sterile container and the supplemental protein is provided in a second sterile container.

Although the agents used in the disclosed invention are preferably non-toxic at the concentrations employed for treatment, it may be desirable to substantially inactivate any residual crosslinking agent with an inactivating agent once adequate crosslinking has been achieved in order to reduce any toxic potential the crosslinking agent may still possess. For example, a diluted solution of glycine will inactivate unreacted gluteraldehyde as described by Aksan (PCT/WO 0170151). Because the inactivating agent can react with the crosslinking agent, in preferred embodiments, the crosslinking agent is provided in first sterile container and the inactivating agent is provided in a second sterile container.

In certain crosslinking procedures, the reaction is reversible, particularly if there is a dramatic change in pH. For these reversible reactions, it may be preferable to add a stabilizing agent once the crosslinking has been achieved. For example, the reaction of aldehyde functional groups with proteins generally forms what is know as a Schiff base, which may be a reversible reaction (with the exception of gluteraldehyde, which may undergo an irreversible reaction with proteins). In these cases where reverse reactions are possible, it may be preferable to include a later step of adding a stabilizing agent that substantially prevents the reversal of the crosslinking reaction. Preferred stabilizing agents comprise boron compounds. More preferred stabilizing agents are selected from the group consisting of sodium borohydride, sodium cyanoborohydride or pyridine borane. Pyridine borane is a more preferred agent for this invention due to its relatively higher biocompatibility. Because the stabilizing agent can react with the crosslinking agent, in preferred embodiments, the crosslinking agent is provided in a first sterile container and the stabilizing agent is provided in a second sterile container.

In some embodiments, one or more of the compounds selected from the group consisting of the crosslinking agent, the supplemental protein, the inactivating agent and the stabilizing agent is delivered (preferably, separately) to the disc in a buffered saline solution capable of controlling pH during the crosslinking reaction. Preferably, the solution is buffered to a pH of approximately 6.5 to 8.0, more preferably between approximately 7.0 to 7.5.

In some embodiments, one or more of the compounds selected from the group consisting of the crosslinking agent, the supplemental protein, the inactivating agent and the stabilizing agent is delivered (preferably, separately) to the disc in a composition further comprising a radio-opaque contrast medium present in an amount sufficient to monitor the flow of the composition through fluoroscopy. In some embodiments, the radio-opaque contrast medium comprises iodine. In some embodiments, the radio-opaque contrast medium is an iodine-containing dye. In some embodiments, the radio-opaque contrast medium comprises a compound selected from the group consisting of barium-containing compounds (such as barium sulfate), zirconia and tantalum, is preferably a barium-containing compound, and more preferably is barium sulfate.

Therefore, in accordance with the present invention, there is provided a composition present within a natural intervertebral disc having a nucleus pulposus and an annulus fibrosus, comprising a crosslinked structure comprising:
  a) proteins Which are native to the intervertebral disc, and
  b) a radio-opaque contrast medium present in an effective amount to be detected by fluoroscopy.

Also in accordance with the present invention, there is provided a composition for treating a natural intervertebral disc having native proteins, the composition comprising:
  a) a crosslinking agent present in an effective amount for crosslinking both at least a portion of the native proteins, and
  b) a radio-opaque contrast medium present in an effective amount to be detected by fluroscopy.

In preferred embodiments, the compound is delivered in a buffered saline solution containing the radio-opaque contrast medium. In more preferred embodiments, each compound used in the procedure is delivered in a buffered saline solution containing the radio-opaque contrast medium.

When certain embodiments of the present invention are practiced, there is produced a composition present within an intervertebral disc having a nucleus pulposus, comprising a crosslinked structure comprising:
  a) proteins which are native to the intervertebral disc, and
  b) supplemental proteins.

In some embodiments, the crosslinked structure further comprises:
  c) a direct crosslinking agent, preferably, gluteraldehyde.

In some embodiments, the native proteins are substantially derived from the nucleus pulposus.

When certain embodiments of the present invention are practiced, there is produced a composition formed within an intervertebral disc having a level of naturally crosslinked proteins, the composition comprising a crosslinked structure comprising proteins which are native to the natural intervertebral disc, wherein the crosslinked structure has a degree of crosslinking which is higher than the unmodified level of naturally crosslinked proteins. Preferably, the naturally crosslinked proteins are unmodified.

In some embodiments, the crosslinked structure further comprises a direct cross linking agent, preferably gluteraldehyde. In others, the crosslinked structure has been crosslinked using an indirect crosslinking agent which is not incorporated into the crosslinked structure. Optionally, the crosslinked structure further comprises supplemental proteins. In preferred embodiments, the disc further comprises an annulus fibrosus having an inner wall, and wherein the crosslinked structure includes the inner wall of the annulus fibrosus. In others, the crosslinked structure is present essentially within the nucleus pulposus. In others, the crosslinked structure is present essentially throughout the entire disc.

In a preferred embodiment of the invention, the agents and materials to be delivered to the intervertebral disc are injected percutaneously under fluoroscopic control using a syringe and appropriate gauge needle, for example 25 G. Such a minimally invasive procedure is highly desirable for minimizing damage to musculoskeletal structures and can be performed using an outpatient procedure. Although this injection can be delivered from any approach to the disc, it is preferable to use a posterior or posterolateral approach such that the needle is required to pass through a shortest distance before reaching the disc without penetrating major vascular or neural structures. Preferably, the agents and materials of this invention are injected into the center of the nucleus pulposus of the disc such that the material can then disperse radially into the remainder of the nucleus pulposus and/or remainder of the disc.

The volume of diluted crosslinking solution injected into the disc is preferably between approximately 0.1 and 10 ml, more preferably between approximately 1 and 5 ml. This ensures that adequate crosslinking agent is delivered to the disc yet does not produce high pressures in the disc, potentially causing failure of the disc and extruding of crosslinking agent and disc material. The volume of supplemental protein needed is preferably determined based on the amount of volume restoration needed to restore the disc to its natural size. This can be determined using a combination of x-rays and MRI scans.

In another preferred embodiment, light exercising is used as an adjunct to the procedure in order to aid in the dispersing of agents and materials within the disc and to ensure complete reaction of the functional materials injected and/or generated. Examples of light exercise include limited left and right lateral bending, flexion and extension, and torso twists (axial rotation). Preferably, the light exercising is performed after each step of the treatment to disperse each agent or material prior to delivering a subsequent material.

As noted above, it is desirable to provide the different compounds used in the present invention in separate sterile containers in order to avoid undesirable reactions therebetween prior to their injection into the disc.

Therefore, in accordance with the present invention, there is provided a kit for injecting therapeutic solutions into an intervertebral disc having native proteins, comprising:

a) a first container having a sterile inner surface and containing a first compound, and b) a second contained having a sterile inner surface and containing a second different compound, wherein the first and second compounds are selected from the group consisting of:
  i) a crosslinking agent present in an effective amount for cross linking at least a portion of the native proteins,
  ii) a supplemental protein,
  iii) an inactivating agent, and
  iv) a stabilizing agent.

In some embodiments, there is provided a third container having a sterile inner surface containing a third different compound selected from the above group of compounds. In other embodiments, there is provided a fourth container having a sterile inner surface containing a fourth different compound selected from the above group of compounds.

In preferred embodiments, at least one container containing a compound further contains a buffered saline solution, and preferably further contains a radio-opaque contrast medium. In more preferred embodiments, each provided container containing a compound further contains a buffered saline solution, and preferably further contains a radio-opaque contrast medium.

In preferred embodiments, the first container contains the crosslinking agent present in an effective amount for crosslinking at least a portion of the native proteins, and the second container contains the supplemental protein.

In some preferred kit embodiments, the crosslinking agent is a direct crosslinking, agent (such as gluteraldehyde) and the supplemental protein is collagen. In others, the crosslinking agent is an indirect cross linking agent (such as sodium periodate) and the supplemental agent is hyaluronan.

In some embodiments, the kit further comprises first and second sterile syringes for separately injecting the compounds. In other embodiments, third and preferably fourth syringes are also provided. In some embodiments, the containers of the kit are provided in a case. Likewise the syringes of the kit are provided in the case.

EXAMPLE 1

Biomechanical Testing of Cadaveric Functional Spine Units after Crosslinking Treatment In a prophetic experiment, four human cadaveric lumbar spine segments (L1–L5) are tested biomechanically to determine range-of-motion (ROM) in flexion-extension, lateral bending, axial torsion and pure compression to establish a baseline. Three crosslinking solutions plus one control solution are prepared: 1) 10% w/v gluteraldehyde in 0.1M phosphate buffered saline (PBS) with pH 7.4; 2) 10% w/v bis(sulfosuccinimidyl suberate) in PBS; 3) 10% sodium periodate in PBS; 4) PBS alone. For a given treatment, 2 ml of solution is injected into the center of one of the four intervertebral discs of the cadaveric lumbar spine using a 5 ml syringe and 25 G needle. For each spine segment, all treatments are applied, one to each level.

Following the injections, the spine segments are subjected to simulated light exercise, i.e. flexion-extension, lateral bending and axial rotation. These exercises are repeated at various times during the course of the experiment. After 2 hours and 24 hours, the biomechanical range of motion (ROM) testing is repeated to measure the effect of crosslinking on each motion segment.

The range of motion testing should indicate that the stiffness of the segments significantly increased over that of a normal untreated disc.

EXAMPLE 2

Outpatient Procedure for In Situ Crosslinking Treatment of the Intervertebral Disc After complaining of low back and leg pain, a patient is referred to a spine specialist. Using x-rays and MRI, the physician determines that the pain is being caused by a bulging intervertebral disc with loss of disc height. The recommended treatment is restoration of disc height with an injection of soluble Type I atelocollagen followed by crosslinking treatment with 10% gluteraldehyde.

In the first outpatient procedure, 2 ml of atelopeptide Type I collagen solution is injected percutaneously into the center of the intervertebral disc. The patient then follows a prescribed light exercise regimen of limited right and left lateral bending, flexion and extension, and torsional twisting and told to refrain from lifting heavy objects and engaging in high impact exercises.

The second outpatient procedure is performed on the following day. In this procedure, 2 ml of 10% gluteraldehyde solution in 0.1 M phosphate buffered saline (pH 7.4) is injected percutaneously into the center of the intervertebral disc. Again, the patient then follows a prescribed light exercise regimen of limited right and left lateral bending, flexion and extension, and tortional twisting and told to refrain from lifting heavy objects and engaging in high impact exercises for at least two days.

We claim:

1. A method of treating in a living being a pathological intervertebral disc having a nucleus pulposus and native molecular proteins, comprising the steps of:

a) injecting a supplemental protein having a reactive aldehyde functional group into the intervertebral disc on a first day, b) allowing or effecting the dispersion of the supplemental protein throughout at least the nucleus pulposus on the first day, and c) injecting the crosslinking agent glutaraldehyde into the intervertebral disc on a following day in an effective amount to cause in-situ crosslinking of at least a portion of the native proteins present in the nucleus pulposus.

2. The method of claim 1 wherein the crossliniking agent is injected in an amount sufficient to crosslink the supplemental protein.

3. The method of claim 2 wherein the supplemental protein is selected from the group consisting of collagen, hyaluronan, chondroitin sulfate, keratan sulfate, albumin, elastin, fibrin, fibronectin and casein.

4. The method of claim 1 wherein the supplemental protein is injected into the nucleus pulposus.

5. The method of claim 1 wherein the crossliniking agent is injected in an amount sufficient to crosslink the supplemental protein with the native proteins.

6. The method of claim 1 wherein the crosslinking agent is injected into the nucleus pulposus.

7. The method of claim 6 wherein the crosslinking agent is injected only into the nucleus pulposus.

* * * * *